(12) United States Patent
Mori

(10) Patent No.: US 11,430,114 B2
(45) Date of Patent: Aug. 30, 2022

(54) LANDMARK ESTIMATING METHOD, PROCESSOR, AND STORAGE MEDIUM

(71) Applicant: OLYMPUS CORPORATION, Tokyo (JP)

(72) Inventor: Junichi Mori, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 169 days.

(21) Appl. No.: 17/093,800

(22) Filed: Nov. 10, 2020

(65) Prior Publication Data
US 2021/0056695 A1 Feb. 25, 2021

Related U.S. Application Data

(63) Continuation of application No. PCT/JP2018/023833, filed on Jun. 22, 2018.

(51) Int. Cl.
*G06T 7/00* (2017.01)
*G06T 7/13* (2017.01)
(Continued)

(52) U.S. Cl.
CPC .......... *G06T 7/0012* (2013.01); *A61B 1/2736* (2013.01); *G02B 23/2484* (2013.01);
(Continued)

(58) Field of Classification Search
CPC G06T 7/0012; G06T 7/13; G06T 7/90; G06T 7/70; G06T 7/60; G06T 2207/10068; G06T 2207/30096; G06T 2207/10024; A61B 1/2736; G02B 23/2484; H04N 5/2253; H04N 7/183; H04N 2005/2255
See application file for complete search history.

(56) References Cited

U.S. PATENT DOCUMENTS 9,599,810 B2 * 3/2017 Matsui ..................... A61B 1/05
9,600,928 B2 * 3/2017 Bendall ..................... G06T 7/50
(Continued)

FOREIGN PATENT DOCUMENTS

EP 1 849 402 A1 10/2007
JP 2009-201682 A 9/2009
(Continued)

OTHER PUBLICATIONS

Khalil, Hesham. "A basic review on the inferior alveolar nerve block techniques." Anesthesia, essays and researches vol. 8, 1 (2014) : 3-8. doi: 10.4103/0259-1162.128891.*
(Continued)

*Primary Examiner* — Shefali D Goradia
(74) *Attorney, Agent, or Firm* — Scully, Scott, Murphy & Presser, P.C.

(57) ABSTRACT

A landmark estimating method estimates a position of a landmark that is a hole existing in an object and is a site through which an insertion portion penetrates, in an endoscope image obtained by picking up an image of the object by an endoscope with the insertion portion bent. The landmark estimating method includes estimating an axis of the insertion portion, estimating a boundary of the insertion portion and the object, and estimating the position of the landmark based on the axis and the boundary that are estimated.

13 Claims, 11 Drawing Sheets

(51) Int. Cl.
  *G06T 7/90* (2017.01)
  *G06T 7/70* (2017.01)
  *A61B 1/273* (2006.01)
  *G02B 23/24* (2006.01)
  *G06T 7/60* (2017.01)
  *H04N 5/225* (2006.01)
  *H04N 7/18* (2006.01)

(52) U.S. Cl.
  CPC .............. *G06T 7/13* (2017.01); *G06T 7/60* (2013.01); *G06T 7/70* (2017.01); *G06T 7/90* (2017.01); *G06T 2207/10024* (2013.01); *G06T 2207/10068* (2013.01); *G06T 2207/30096* (2013.01); *H04N 5/2253* (2013.01); *H04N 7/183* (2013.01); *H04N 2005/2255* (2013.01)

(56) References Cited

U.S. PATENT DOCUMENTS

| | | | | |
|---|---|---|---|---|
| 10,159,401 | B2* | 12/2018 | Yamaya | H04N 5/2256 |
| 2009/0208071 | A1 | 8/2009 | Nishimura et al. | |
| 2011/0015486 | A1* | 1/2011 | Yamamoto | H04N 13/363 |
| | | | | 600/109 |
| 2011/0299748 | A1 | 12/2011 | Nishimura et al. | |
| 2012/0078045 | A1 | 3/2012 | Sasaki et al. | |
| 2014/0362199 | A1* | 12/2014 | Popovic | A61B 90/11 |
| | | | | 348/65 |
| 2015/0009311 | A1 | 1/2015 | Sasaki et al. | |
| 2017/0337705 | A1* | 11/2017 | Bendall | G01B 11/24 |
| 2018/0263527 | A1* | 9/2018 | Kitamura | A61B 1/0005 |
| 2019/0206281 | A1* | 7/2019 | Dantes | G09B 23/28 |

FOREIGN PATENT DOCUMENTS

| | | |
|---|---|---|
| JP | 2012-070938 A | 4/2012 |
| JP | 2016-080674 A | 5/2016 |
| WO | 2006/087981 A1 | 8/2006 |
| WO | WO-2015043793 A1 * 4/2015 ........... A61B 5/0077 |

OTHER PUBLICATIONS

Chu, Yakui, et al. "Registration and fusion quantification of augmented reality based nasal endoscopic surgery." Medical image analysis 42 (2017): 241-256.*

International Search Report dated Sep. 18, 2018 received in PCT/JP2018/023833.

* cited by examiner

LANDMARK ESTIMATING METHOD, PROCESSOR, AND STORAGE MEDIUM

CROSS REFERENCE TO RELATED APPLICATION

This application is a continuation application of PCT/JP2018/023833 filed on Jun. 22, 2018, the entire contents of which are incorporated herein by this reference.

BACKGROUND OF THE INVENTION

1. Field of the Invention

The present invention relates to a landmark estimating method, a processor, and a storage medium.

2. Description of the Related Art

Conventionally, endoscopes have been widely used in the medical field and the industrial field. For example, in the medical field, a surgeon can look at an endoscope image of an inside of a subject that is displayed on a display apparatus, find and identify a lesion part that is an object, and perform a treatment on the lesion part using a treatment instrument.

There is generally known a technology that calculates three-dimensional coordinates of an object by using the principle of triangulation, based on misalignment information of a plurality of images obtained from different viewpoints. There is also known a technology that irradiates an object with a projected light, and obtains three-dimensional coordinates of the object based on a time period until a reflection light reaches a sensor, a pattern the image of which is picked up, or the like.

By obtaining three-dimensional coordinates of two points or more of an object by using the above technologies, physical quantities such as a size and a volume of the object are calculated. In observation by an endoscope, it is possible to measure the size of a tumor, a distance from a spot that is a landmark such as a cardia and an anus to the tumor, and the like by using the above technologies.

It is necessary to set a measurement point and a measurement area when calculating the physical quantities of an object. When the distance from the landmark to the tumor is measured in endoscope observation as described above, it is necessary to properly set the position of the landmark and the position of the tumor.

When a tumor exists in a vicinity of a cardia or an anus that is the landmark, it is necessary to bend an endoscopic scope, and photograph the object in a posture with the distal end portion turning around. When the object is photographed in the posture, the endoscopic scope itself is reflected in the endoscope image. Accordingly, it is not possible to directly photograph the landmark by the reflected endoscopic scope, and therefore it is difficult to properly set the measurement point. Thus, there is proposed a method for indirectly estimating a measurement point.

For example, by using the method proposed in Japanese Patent Application Laid-Open Publication No. 2016-80674, it is possible to indirectly estimate a measurement point by setting a region of interest containing the measurement point that is difficult to directly specify, and analyzing the region of interest.

SUMMARY OF THE INVENTION

A landmark estimating method of one aspect of the present invention is a landmark estimating method for estimating a position of a landmark that is a hole existing in an object and is a site through which an insertion portion penetrates, in an endoscope image obtained by picking up an image of the object by an endoscope with the insertion portion bent, the method including estimating an axis of the insertion portion, estimating a boundary of the insertion portion and the object, and estimating the position of the landmark based on the axis and the boundary.

A processor of one aspect of the present invention estimates a position of a landmark that is a hole existing in an object and is a site through which an insertion portion penetrates, in an endoscope image obtained by picking up an image of the object by an endoscope with the insertion portion bent, and includes an axis estimation circuit configured to estimate an axis of the insertion portion, a boundary estimation circuit configured to estimate a boundary of the insertion portion and the object, and a landmark position estimation circuit configured to estimate the position of the landmark based on the axis and the boundary.

A storage medium of one aspect of the present invention is a non-transitory computer-readable storage medium storing a program. The program is a program for estimating a position of a landmark that is a hole existing in an object and is a site through which an insertion portion penetrates, in an endoscope image obtained by picking up an image of the object by an endoscope with the insertion portion bent. The program is configured to cause a computer to estimate an axis of the insertion portion, estimate a boundary of the insertion portion and the object, and estimate the position of the landmark based on the axis and the boundary.

DETAILED DESCRIPTION OF THE PREFERRED EMBODIMENTS

Hereinafter, embodiments will be described with reference to the drawings.

First Embodiment

Figure 1:
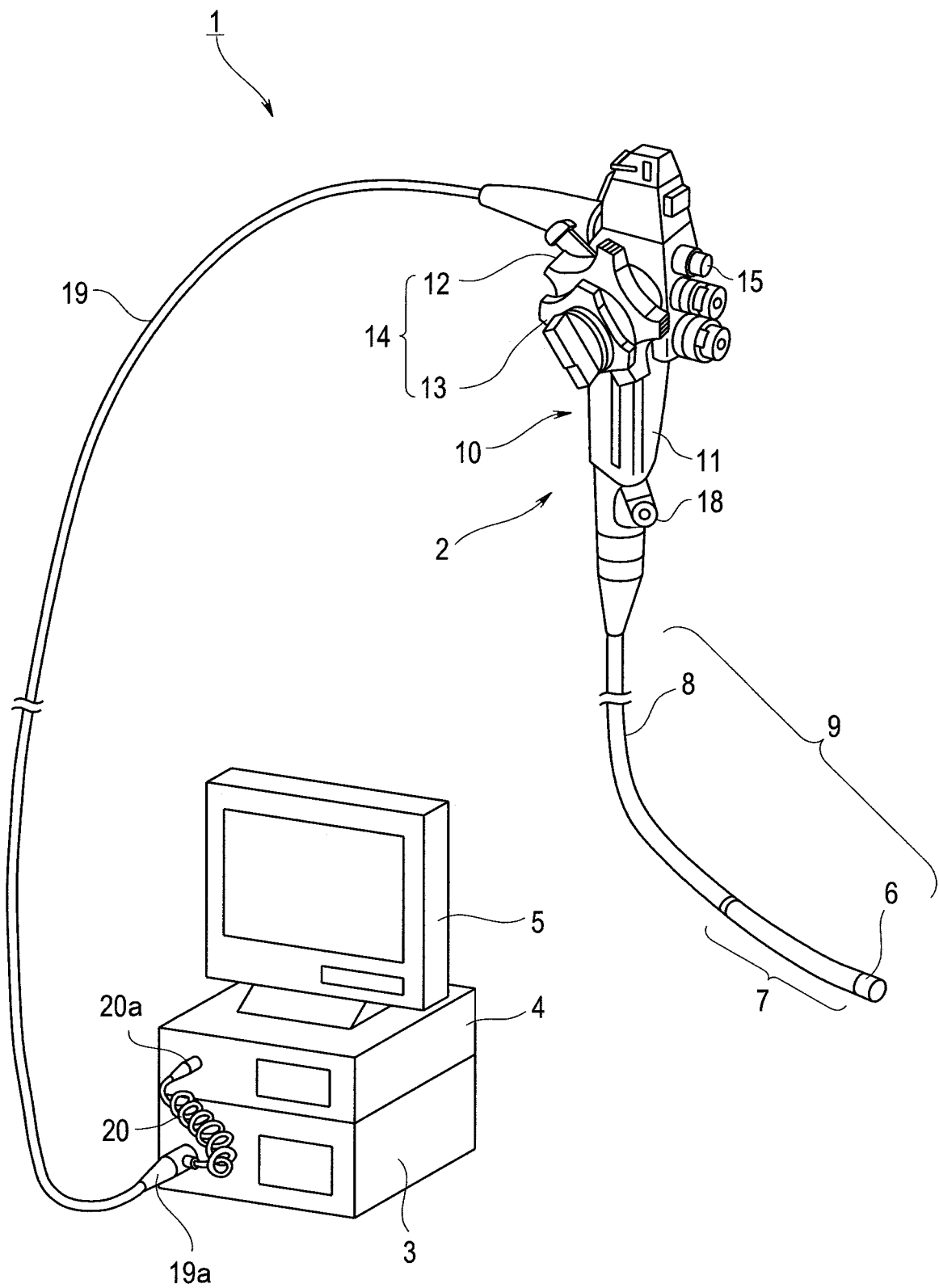
FIG. 1 is a perspective view illustrating one example of an entire configuration of an endoscope apparatus 1 according to an embodiment of the present invention.

FIG. 1 is a perspective view illustrating one example of an entire configuration of an endoscope apparatus according to an embodiment of the present invention. As illustrated in FIG. 1, an endoscope apparatus 1 of the present embodiment is mainly configured by an electronic endoscope (hereinafter, simply referred to as an endoscope) 2, a light source apparatus 3, a processor 4, and a monitor 5.

The endoscope 2 is configured by having an elongated insertion portion 9 having a long length, an operation portion 10, and a universal cable 19 that is an electric cable. The insertion portion 9 of the endoscope 2 is configured by having a distal end portion 6, a bending portion 7, and a flexible tube portion 8 in order from a distal end. An illumination window and an observation window not illustrated are provided in the distal end portion 6, an illumination light is emitted to a subject from the illumination window, and a return light from the subject is incident on the observation window. In the distal end portion 6, a solid image pickup device such as a CCD or a CMOS is disposed as means that picks up an image of an object, and photoelectrically converts an object image by the light incident from the observation window to output an image pickup signal. The image pickup signal is supplied to the processor 4 via the universal cable 19.

In the operation portion 10, a bending operation portion 14 is rotatably placed, and switches of various endoscope functions and the like are provided. The bending operation portion 14 is configured to perform a bending operation of the bending portion 7 of the insertion portion 9, and the switches include a focus switch 15. Note that in the bending operation portion 14, a UD bending operation knob 12, and an RL bending operation knob 13 are placed to be superimposed on each other. The UD bending operation knob 12 is configured to perform a bending operation of the bending portion 7 in an up-down direction, and the RL bending operation knob 13 is configured to perform a bending operation of the bending portion 7 in a left-right direction.

A connection portion of the insertion portion 9 and the operation portion 10 is configured by having a grasping portion 11, and a treatment instrument channel insertion portion 18. The grasping portion 11 serves as a grasping portion by a user. The treatment instrument channel insertion portion 18 is placed in a bend preventing portion provided between the grasping portion 11 and one end of the flexible tube portion 8 of the insertion portion 9, and is an opening portion of a treatment instrument channel that is placed in the insertion portion 9 and allows various treatment parts to be inserted through the treatment instrument channel.

The universal cable 19 that is extended from the operation portion 10 has a scope connector 19a that is attachable to and detachable from the light source apparatus 3, at an extension end. At the scope connector 19a, a coil-shaped coil cable 20 is extensively provided, and at an extension end of the coil cable 20, a scope connector 20a is provided. The scope connector 20a is a connector that is attachable to and detachable from the processor 4. Note that the endoscope 2 of the present embodiment transmits an illumination light from the light source apparatus 3 to the distal end portion 6 by a light guide cable of illumination means that is placed in the universal cable 19, the operation portion 10, and the insertion portion 9.

The processor 4 is electrically connected to the monitor 5 that displays an endoscope image. The processor 4 processes an image pickup signal that is photoelectrically converted by image pickup means such as a CCD mounted on the endoscope 2, and outputs the image pickup signal to the monitor 5 as an image signal. On the monitor 5, an endoscope image is displayed.

Figure 2:
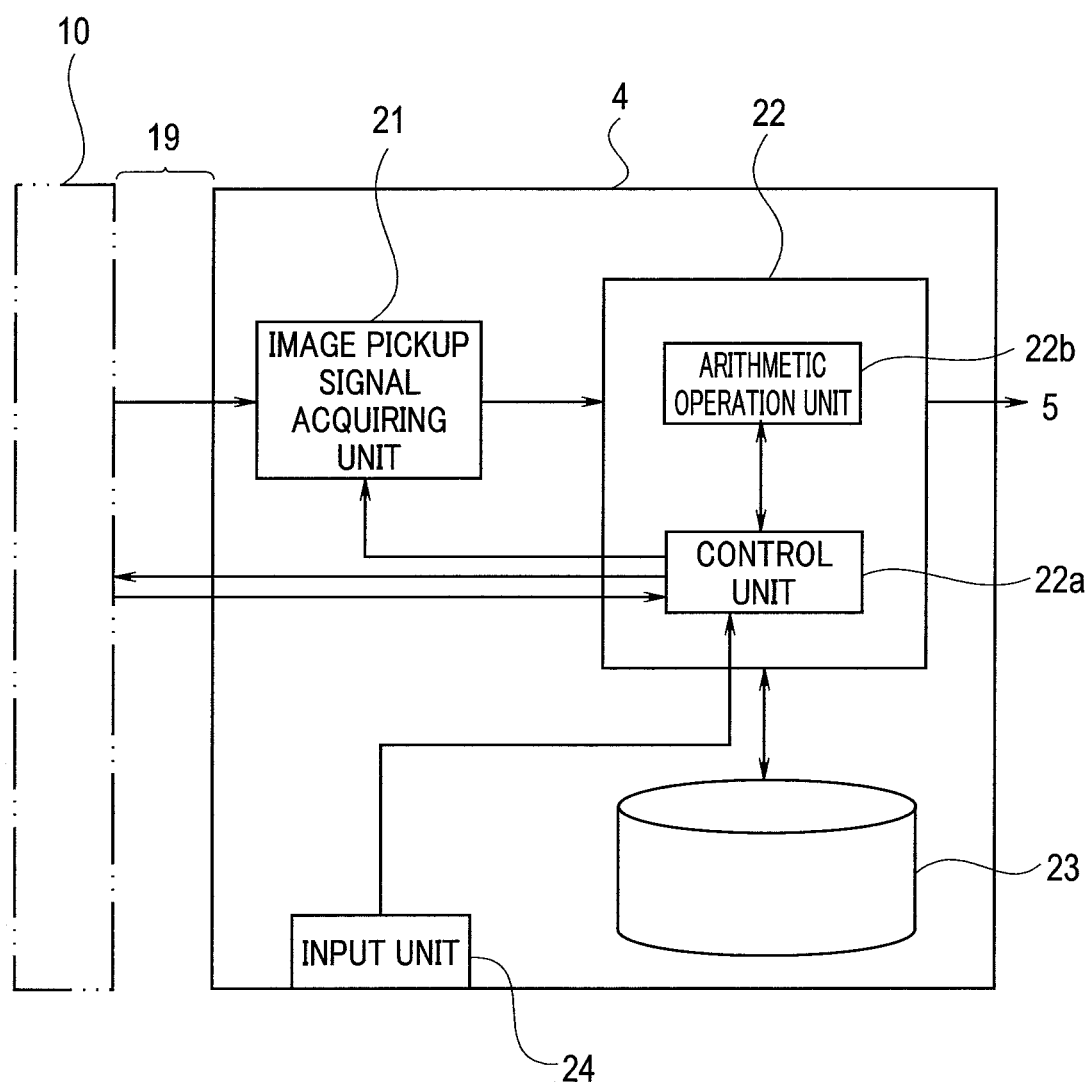
FIG. 2 is a block diagram illustrating a configuration relating to image processing of a processor 4 according to a first embodiment of the present invention.

FIG. 2 is a block diagram illustrating a configuration relating to image processing of the processor 4. The processor 4 is an image processing apparatus having an image pickup signal acquiring unit 21, a control arithmetic operation unit 22, a storage apparatus 23, and an input unit 24. The control arithmetic operation unit 22 is a circuit including a control unit 22a, and an arithmetic operation unit 22b.

The image pickup signal acquiring unit 21 is a circuit that receives and acquires an image pickup signal from the image pickup device of the endoscope 2, and outputs the image pickup signal to the control arithmetic operation unit 22, under control of the control unit 22a.

The control unit 22a includes a central processing unit (hereinafter, referred to as a CPU), a ROM, a RAM, and the like, and performs control of an operation of the entire processor 4. The control unit 22a also performs control of drive of the image pickup device of the endoscope 2, control of various circuits based on various operation signals from the operation portion 10 of the endoscope 2, control of recording of various data to the storage apparatus 23 and reading of various data from the storage apparatus 23, and control of image processing, in response to an instruction to the input unit 24 by a surgeon.

In other words, the control unit 22a controls an operation of the endoscope apparatus 1, and outputs control signals or setting signals to respective units based on an instruction or an input that are performed through the input unit 24.

The arithmetic operation unit 22b is a circuit that executes various kinds of image processing and various kinds of arithmetic operation processing, generates an image signal of an endoscope image and various display information that are displayed on the monitor 5, and outputs the image signal and the various display information to the monitor 5, based on the image pickup signal acquired in the image pickup signal acquiring unit 21, under control of the control unit 22a.

Note that all or a part of the processes of the control unit 22a and the arithmetic operation unit 22b in the control arithmetic operation unit 22 may be performed by a program stored in a non-transitory computer-readable storage medium.

The storage apparatus 23 is a storage apparatus of a large capacity such as a hard disk apparatus, and stores image data of an endoscope image of an inside of a subject obtained in an endoscopy, and various data such as support information.

The input unit 24 is an operation panel having various buttons, and is an input apparatus for a surgeon to give various settings of the endoscope apparatus 1, various instructions and the like to the processor 4.

Figure 3A:
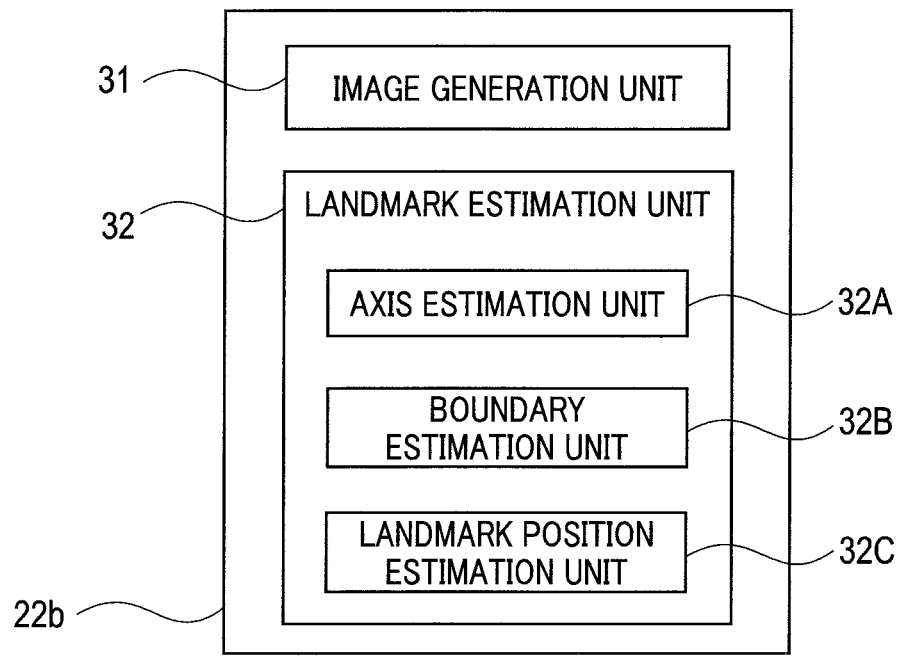
FIG. 3A is a block diagram illustrating a configuration of an arithmetic operation unit 22b of a control arithmetic operation unit 22 according to the first embodiment of the present invention.

FIG. 3A is a block diagram illustrating a configuration of the arithmetic operation unit 22b of the control arithmetic operation unit 22 in the present embodiment.

The arithmetic operation unit 22b is a circuit including an image generation unit 31, and a landmark estimation unit 32.

The image generation unit 31 is a circuit configured to receive an image pickup signal, and generate an endoscope image based on the image pickup signal, in response to an observation mode. The image generation unit 31 performs predetermined emphasis processing, various kinds of correction processing, superimposition processing to superimpose and display various information, a menu screen, and the like, to the endoscope image.

The landmark estimation unit 32 is a circuit configured to estimate a position of a landmark that is a hole (for example, a part of a lumen such as a pyloric portion of a stomach in a gastroenterological endoscopy) through which the insertion portion 9 of the endoscope 2 is inserted into an observation site in an endoscope image. The landmark estimation unit 32 is configured by an axis estimation unit 32A, a boundary estimation unit 32B, and a landmark position estimation unit 32C.

Figure 3B:
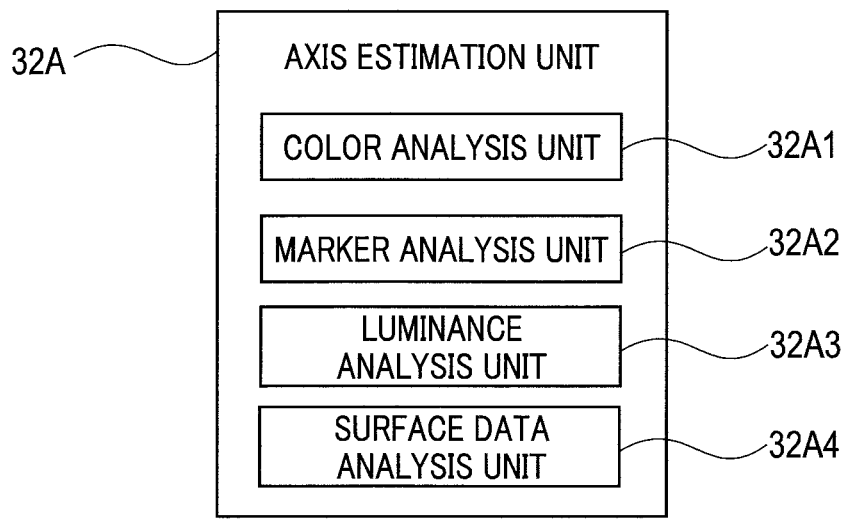
FIG. 3B is a block diagram illustrating a configuration of an axis estimation unit 32A.

The axis estimation unit 32A is a circuit configured to extract the insertion portion 9 of the endoscope 2 from an endoscope image, and estimate a center axis of the insertion portion 9. FIG. 3B is a block diagram illustrating a configuration of the axis estimation unit 32A. Operations of respective units in the axis estimation unit 32A illustrated in FIG. 3B will be described later in corresponding passages in explanation described below. FIG. 3B illustrates not only components according to the present embodiment described later, but also components according to a second to a sixth embodiments that will be described after the present embodiment.

The boundary estimation unit 32B is a circuit configured to estimate an insertion source side (a proximal end side, a side far from the distal end portion 6) as a boundary in the insertion portion 9 that is reflected in an endoscope image.

The landmark position estimation unit 32C is a circuit configured to estimate a position of a landmark by using the estimated center axis of the insertion portion 9 of the endoscope 2, and the estimated boundary of the insertion portion 9 and the object.

Figure 4:
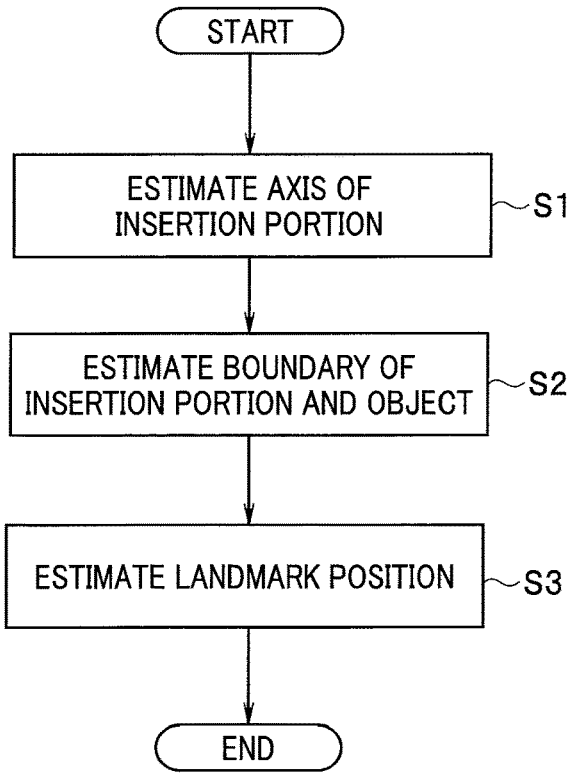
FIG. 4 is a flowchart illustrating one example of a flow of landmark estimation processing in a landmark estimation unit 32.
Figure 5:
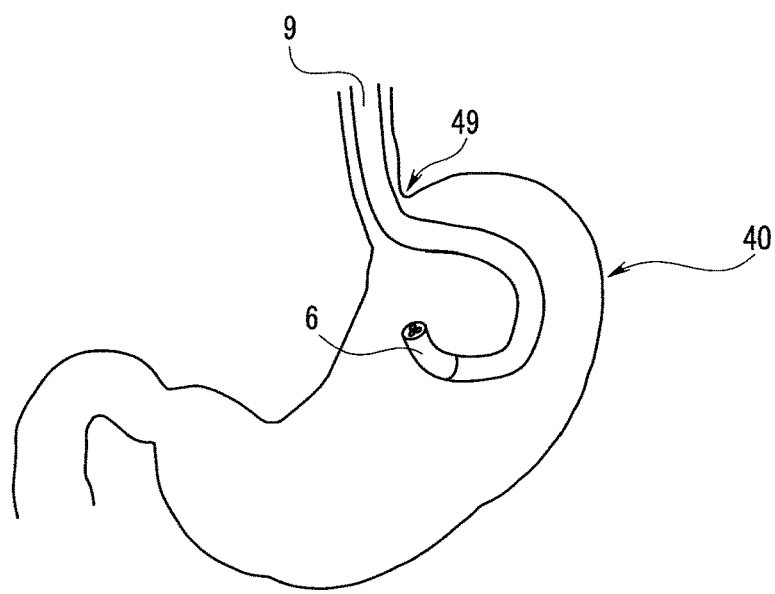
FIG. 5 is a schematic view illustrating one example of a landmark that is an estimation target.

FIG. 4 is a flowchart illustrating one example of a flow of landmark estimation processing in the landmark estimation unit 32. FIG. 5 is a schematic view illustrating an example of a landmark that is an estimation target. As a situation where the insertion portion 9 of the endoscope 2 is bent, and an object is photographed in a posture with the distal end portion 6 turning around, there are cited a case of observing a tumor in a vicinity of an anus portion of a large intestine, an inspection of an access port of an aircraft engine in an industrial endoscope, and the like, in addition to the case of observing a tumor in a vicinity of a cardia portion 49 of a stomach 40 as illustrated in FIG. 5. In the case of FIG. 5, the cardia portion 49 that is the hole through which the insertion portion 9 is inserted to an inside of the stomach is a landmark.

Figure 6A:
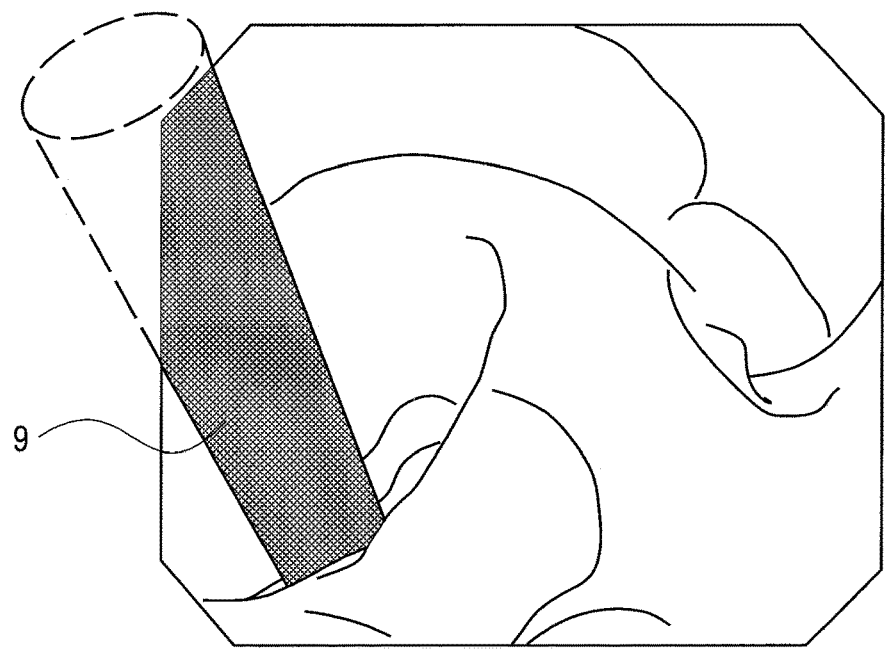
FIG. 6A is a view illustrating one example of an endoscope image generated by an image generation unit 31.

Prior to the landmark estimation processing, the control unit 22a controls drive of the light source and drive of the image pickup device of the endoscope 2, and controls the image pickup signal acquiring unit 21, and thereby the arithmetic operation unit 22b acquires an image pickup signal from the endoscope 2. The image generation unit 31 of the arithmetic operation unit 22b generates an endoscope image based on the image pickup signal, under control of the control unit 22a. FIG. 6A is a view illustrating one example of the endoscope image generated by the image generation unit 31.

The landmark estimation unit 32 firstly estimates an axis of the insertion portion 9 based on the generated endoscope image (step S1). The axis estimation unit 32A in FIG. 3A is involved in processing of S1. The axis can be estimated by extracting the insertion portion 9 that is an entity, from the endoscope image, for example, and identifying a longitudinal direction of the insertion portion 9 from a shape of the insertion portion 9. The entity is a component that is extracted from the endoscope image to be used in estimation of the axis.

Subsequently, the landmark estimation unit 32 estimates a boundary of the extracted insertion portion 9 and an object (step S2). The boundary estimation unit 32B in FIG. 3A is involved in processing of S2. When the object is photographed in the posture with the distal end portion 6 turning around, a distal end side of the insertion portion 9 is always located at a periphery side of the endoscope image, and an insertion source side of the insertion portion 9 is always located at a center side of the endoscope image. Accordingly, it is possible to estimate a boundary line that intersects a longitudinal direction of the insertion portion 9 and is located at the center side of the endoscope image as the boundary of the insertion portion 9 and the object, in a boundary line between the insertion portion 9 and the object (an inner wall of a stomach in the case of FIG. 5) on the image.

Figure 6B:
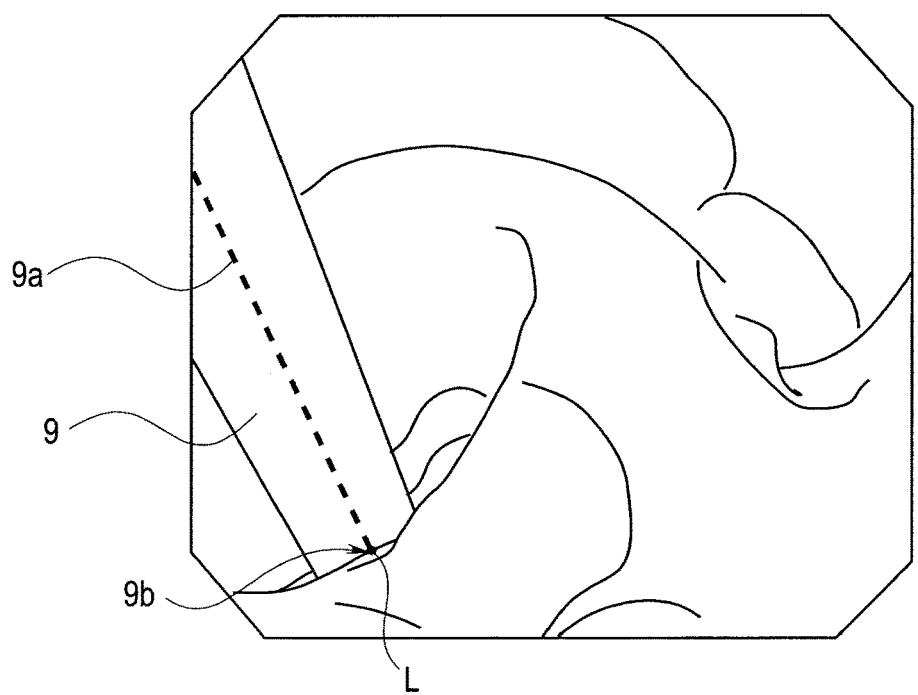
FIG. 6B is a schematic view explaining a landmark position estimated based on the endoscope image in FIG. 6A.

Finally, the landmark estimation unit 32 estimates a position of the landmark (step S3). The landmark position estimation unit 32C in FIG. 3A is involved in processing of S3. FIG. 6B is a schematic view explaining the landmark position estimated based on the endoscope image in FIG. 6A. It is possible to estimate the position of a landmark L as an intersection point of an axis 9a of the insertion portion 9 estimated in S1, and a boundary 9b estimated in S2.

As above, according to the landmark estimating method of the aforementioned embodiment, it is possible to estimate the position of the landmark with high precision even when the landmark is shielded and cannot be directly specified as a measurement point because the endoscope insertion portion is bent and thereby the insertion portion itself is reflected in the endoscope image.

Second Embodiment

In the aforementioned first embodiment, the axis 9a of the insertion portion 9 is estimated by specifying the longitudinal direction of the insertion portion 9, but in a present embodiment, an axis 9a is estimated by using image processing. An endoscope apparatus of the present embodiment has similar components to the components of the endoscope apparatus 1 of the first embodiment, the same components will be assigned with the same reference signs, and explanation will be omitted. Landmark estimation processing of the present embodiment is performed in a similar procedure to the flowchart illustrated in FIG. 4. However, a specific method in S1 differs from the method in S1 of the first embodiment. Hereinafter, the method in S1 in FIG. 4 according to the present embodiment, that is, a specific method for estimating the axis 9a of an insertion portion 9 will be described. Note that a color analysis unit 32A1 in FIG. 3B is involved in processing of S1 in the present embodiment.

Figure 7:
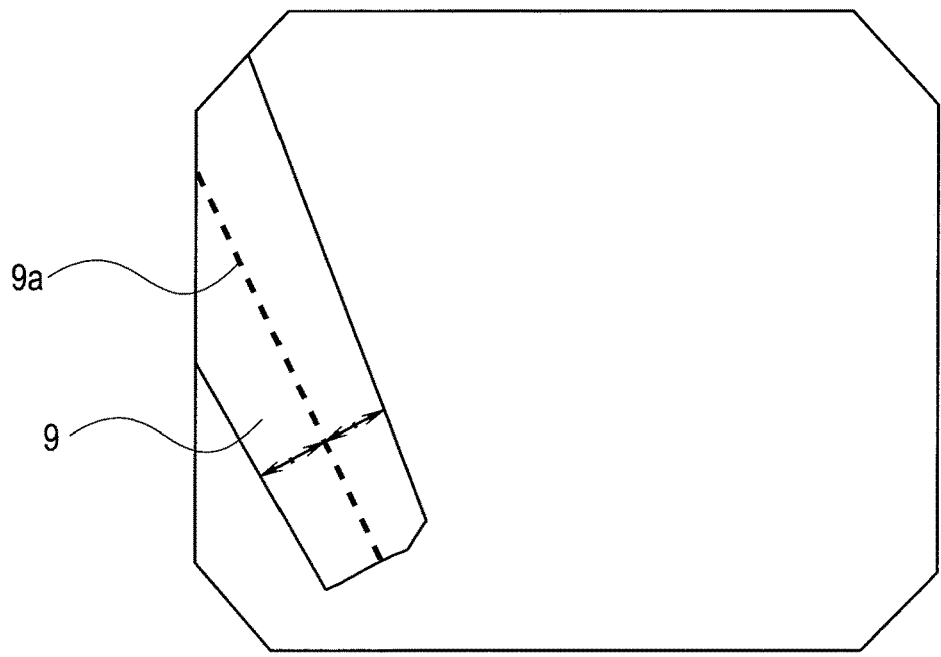
FIG. 7 is a schematic view explaining an axis 9a estimation position of an insertion portion 9 according to a second embodiment.

FIG. 7 is a schematic view explaining an axis 9a estimation position of the insertion portion 9 according to the second embodiment. FIG. 7 illustrates a state in which processing described later is applied to the endoscope image illustrated in FIG. 6A, and an edge (outer edge) of the insertion portion 9 is extracted. In estimating the axis 9a of the insertion portion 9, the color analysis unit 32A1 of the axis estimation unit 32A divides an insertion portion 9 region and a body cavity region by using color analysis of the endoscope image, that is, a difference between a color of the insertion portion 9 (for example, black) and a color of an inside of a body cavity (red), and extracts an edge of the insertion portion 9 as an entity. In edge extraction, an existing method such as Hough transform can be used.

Based on the extracted edge, a straight line (center line) that bisects a width in a radial direction of the insertion portion 9 and is in a longitudinal direction of the insertion portion 9 is calculated. In calculation of the center line, an existing method such as main axis extraction by an image moment may be used. The center line obtained in this way is estimated as the axis 9a of the insertion portion 9.

As above, according to the present embodiment, it is also possible to obtain a similar effect to the effect of the first embodiment.

(Modification of Second Embodiment)

In the aforementioned second embodiment, the axis 9a of the insertion portion 9 is estimated by extracting the edge of the insertion portion 9 by color analysis, but in a present modification, an axis 9a is estimated by using a marker provided on an insertion portion 9 as an entity. An endoscope apparatus of the present modification has similar components to the components of the endoscope apparatus 1 of the first embodiment, the same components will be assigned with the same reference signs, and explanation will be omitted. Landmark estimation processing of the present embodiment is performed in a similar procedure to the flowchart illustrated in FIG. 4. However, a specific method in S1 differs from the method in S1 of the second embodiment. Hereinafter, the method of S1 in FIG. 4 according to the present modification, that is, the specific method for estimating the axis 9a of the insertion portion 9 will be described. Note that a marker analysis unit 32A2 in FIG. 3B is involved in processing of S1 in the present modification.

Figure 8:
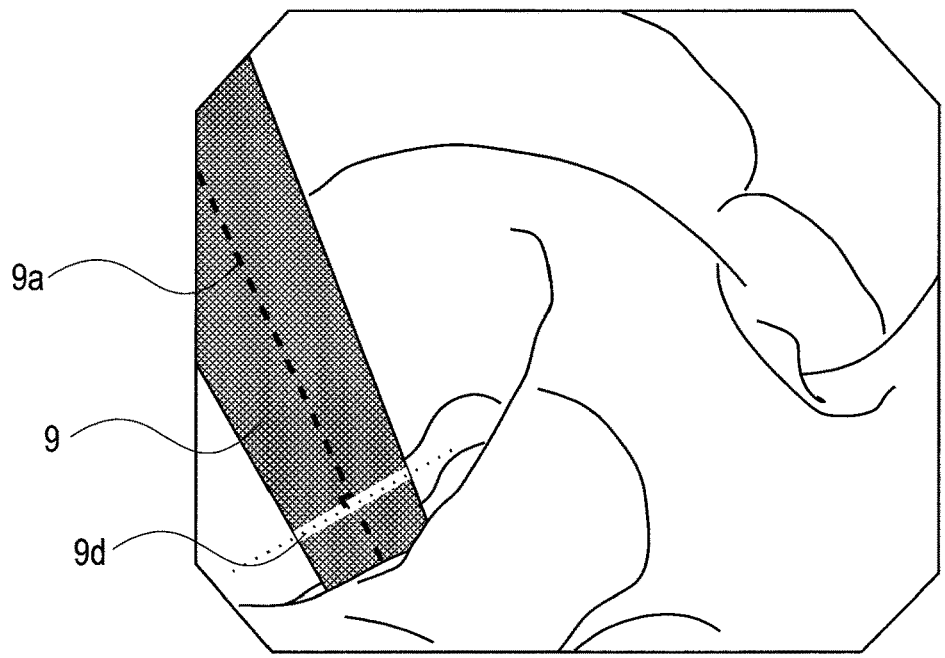
FIG. 8 is a schematic view explaining an axis 9a estimation position of an insertion portion 9 according to a modification of the second embodiment.

FIG. 8 is a schematic view explaining an axis 9a estimation position of the insertion portion 9 according to the modification of the second embodiment. In general, on the insertion portion 9 of an endoscope 2, markers 9d are provided at a constant position (or at a constant interval) from a distal end. As the marker 9d, a marker in a different color from a color of the insertion portion 9 is provided so as to be easily recognized on an endoscope image. For example, when the color of the insertion portion 9 is black, the marker 9d in white that is an opposite color is provided. The marker 9d is desirably disposed so that the marker 9d is always recognizable on the endoscope image regardless of an insertion state of the insertion portion 9, such as an insertion direction, and an insertion depth/orientation of insertion. Accordingly, for example, the markers 9d in a shape to go around an outer edge in a radial direction of the insertion portion 9 are disposed at a constant interval from a distal end.

The marker analysis unit 32A2 of the axis estimation unit 32A extracts the markers 9d from the endoscope image based on information concerning a shape and the color of the marker stored in advance in the storage apparatus 23 or the like. When the markers 9d in such a shape as to go around the outer edge in the radial direction of the insertion portion 9 are provided as described above, a direction that is orthogonal to a line segment extracted as the markers 9d is estimated as an axial direction. Note that the estimating method of the axis differs according to the shape of the markers 9d. For example, when the marker 9d having a shape of a straight line with scales added at constant intervals, such as a number line, is disposed in a longitudinal direction of the insertion portion 9, a same direction as the marker 9d is estimated as the axial direction.

As above, according to the present modification, it is also possible to obtain similar effects to the effects of the first and the second embodiments.

Third Embodiment

In the aforementioned embodiments, the entities such as the longitudinal direction, the edge, and the marker of the insertion portion 9 are extracted from the endoscope image, and the axis 9a is estimated based on the information on these entities, but a present embodiment differs from the aforementioned embodiments in that an axis 9a is estimated by also using luminance information of an image. An endoscope apparatus of a present embodiment has similar components to the components of the endoscope apparatus 1 of the first embodiment, the same components will be assigned with the same reference signs, and explanation will be omitted. Landmark estimation processing of the present embodiment is performed in a similar procedure to the flowchart illustrated in FIG. 4. However, a specific method in S1 differs from the method in S1 of the second embodiment. Hereinafter, the method in S1 in FIG. 4 according to the present embodiment, that is, a specific method for estimating the axis 9a of an insertion portion 9 according to the present embodiment will be described. Note that a luminance analysis unit 32A3 in FIG. 3B is involved in the processing of S1 in the present embodiment.

Figure 9:
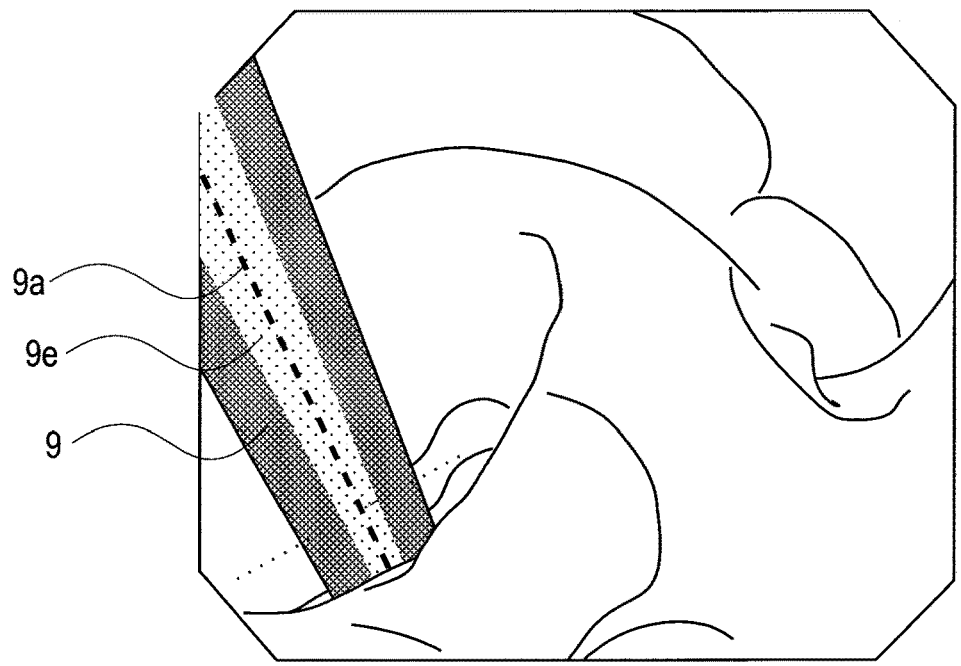
FIG. 9 is a schematic view explaining an axis 9a estimation portion of an insertion portion 9 according to a third embodiment.

FIG. 9 is a schematic view explaining an axis 9a estimation position of the insertion portion 9 according to the third embodiment. The luminance analysis unit 32A3 calculates luminance values of respective pixels in the endoscope image illustrated in FIG. 6A. Normally, mirror surface treatment is applied to a surface of the insertion portion 9. Accordingly, an illumination light irradiated to an inside of a body cavity is specularly reflected on the surface of the insertion portion 9. Since the insertion portion 9 is substantially cylindrical, a reflection angle becomes smaller as specular reflection takes place closer to the axis 9a of the insertion portion 9, and a reflection light is incident perpendicularly onto an image pickup surface disposed on the distal end portion 6. On the other hand, as specular reflection takes place farther from the axis 9a of the insertion portion and closer to an edge, an incident angle of the reflection light increases, and a reflection light is incident on the image pickup surface disposed on the distal end portion 6 with an inclination.

In other words, in the endoscope image, pixels located closer to the axis 9a of the insertion portion 9 have higher luminance values, and pixels farther from the axis 9a have lower luminance values. By using the phenomenon, it is possible to extract a specular reflection part of the insertion portion, that is, a region in which a calculated pixel value is larger than a predetermined threshold by luminance analysis of the endoscope image, and estimate a center region (a high luminance region 9e) of the insertion portion where the axis 9a of the insertion portion 9 exists. A shape of the high luminance region 9e that is an entity is analyzed, and the axis 9a is estimated.

In this way, by using the specular reflection, it is also possible to estimate the axis 9a stably even in a situation where an image of an original texture is not picked up (for example, when a color difference between the insertion portion 9 and an inside of a body cavity is small, and regional division by color is difficult, or when the marker 9d set at the insertion portion 9 is difficult to extract). Note that the luminance analysis unit 32A3 may be used to determine whether or not the axes 9a estimated according to the aforementioned embodiments and modification exist in high luminance regions. In this case, it is possible to eliminate the axis 9a that is erroneously estimated, and therefore, estimation precision of the axis 9a is improved.

As above, according to the present embodiment, it is also possible to obtain a similar effect to the effects of the first and second embodiments. It is possible to improve estimation precision of the axis 9a by further combining the present embodiment with the first and second embodiments.

Fourth Embodiment

In the aforementioned embodiment, the landmark is estimated based on the two-dimensional endoscope image, but in a present embodiment, a three-dimensional endoscope image (3D surface data) is acquired, and based on the three-dimensional endoscope image, a landmark is estimated. An endoscope apparatus of the present embodiment has similar components to the components of the endoscope apparatus 1 of the first embodiment other than means that is provided in an endoscope 2 and configured to acquire 3D surface data, the same components will be assigned with the same reference signs, and explanation will be omitted.

Figure 10:
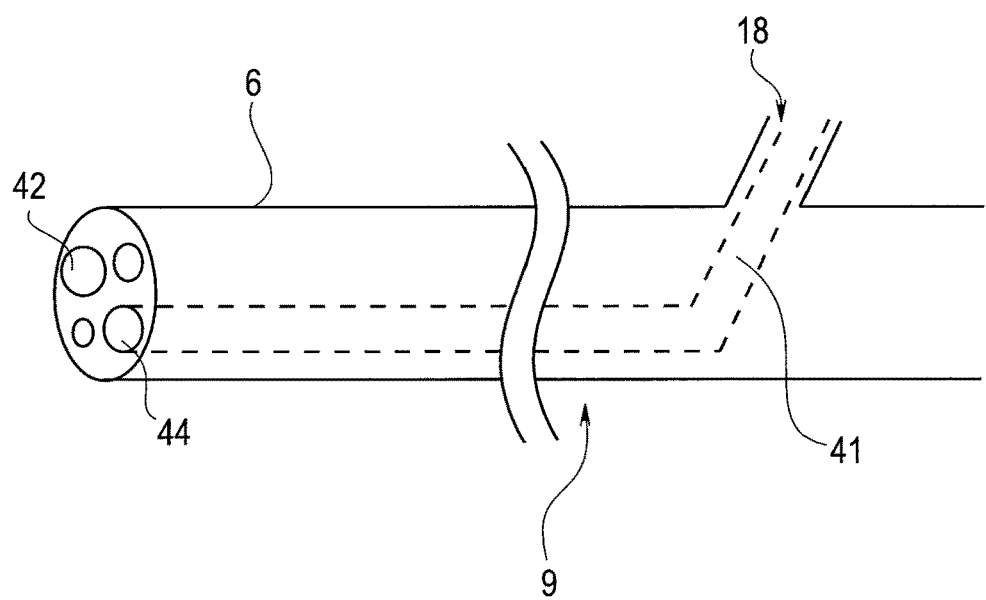
FIG. 10 is a schematic view explaining one example of a configuration of an endoscope 2 according to a fourth embodiment.

FIG. 10 is a schematic view explaining an example of a configuration of the endoscope 2 according to the present embodiment. The endoscope 2 of the present embodiment includes a projection type measurement device 41 as the means for acquiring 3D surface data. The projection type measurement device 41 uses a TOF (time of flight) method. In other words, the projection type measurement device 41 irradiates an object with a projection light, detects a reflection light from the object, measures a time period after the projection light is irradiated until the reflection light is detected, and thereby, calculates three-dimensional coordinates of the object based on the measured time period.

The projection type measurement device 41 is inserted from the treatment instrument channel insertion portion 18, for example, passes through insides of the operation portion 10 and the insertion portion 9, and irradiates the object with the projection light from the treatment instrument channel 44 provided in a distal end portion 6. The reflection light from the object is incident from the treatment instrument channel 44, is detected by a detection unit not illustrated of the projection type measurement device 41, and a time period required until detection is measured. Note that the reflection light from the object may be configured to be detected via the window that is provided in the distal end portion 6 and other than the treatment instrument channel 44. The reflection light may be configured to be detected by an image pickup device via an observation window 42, for example.

Note that the projection type measurement device 41 may be a device using any method as long as the device can acquire 3D surface data without contact. The projection type measurement device 41 may be a device using another method such as a pattern projection method (method that projects a specific known pattern such as a grid pattern to an object, and calculates three-dimensional surface data of the object based on a distortion of the pattern an image of which is picked up by an image pickup device) instead of calculating the three-dimensional coordinates from a return time period of a reflection light as described above.

Figure 11:
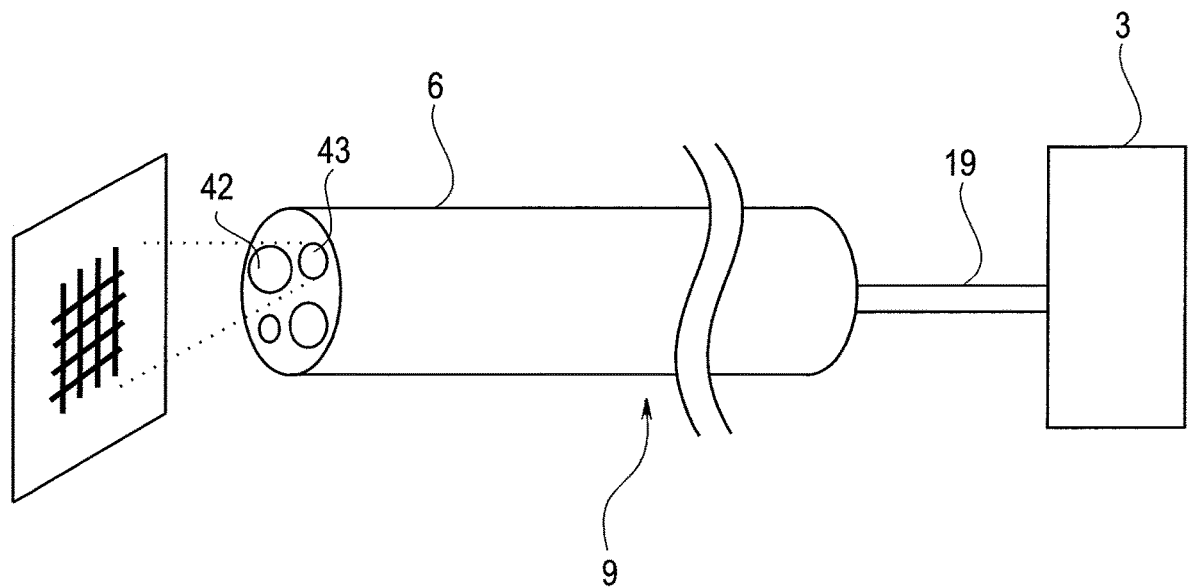
FIG. 11 is a schematic view explaining another example of the configuration of the endoscope 2 according to the fourth embodiment.

The projection light and the specific pattern for measurement may be configured to be irradiated onto the object via an illumination window 43 from a light source apparatus 3, as illustrated in FIG. 11. FIG. 11 is a schematic view explaining another example of the configuration of the endoscope 2 according to the fourth embodiment.

Figure 12:
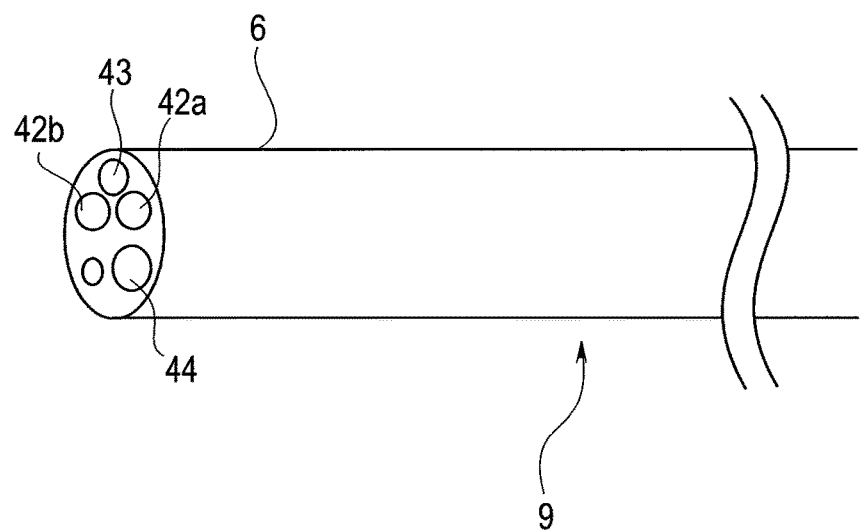
FIG. 12 is a schematic view explaining another example of the configuration of the endoscope 2 according to the fourth embodiment.

As illustrated in FIG. 12, a stereo image pickup system is mounted on the endoscope 2, and 3D surface data of an object may be calculated by using the principle of triangulation, based on misalignment information of two images that are obtained based on reflection lights of the object that are received by two observation windows 42a and 42b at different positions. FIG. 12 is a schematic view explaining another example of the configuration of the endoscope 2 according to the fourth embodiment.

Landmark estimation processing of the present embodiment is performed in a similar procedure to the flowchart illustrated in FIG. 4. However, specific methods of S1 and S3 differ from the methods of the aforementioned embodiments. Hereinafter, the method of S1 in FIG. 4 according to a present embodiment, that is, a specific method for estimating an axis 9a of an insertion portion 9 will be described. Note that a surface data analysis unit 32A4 in FIG. 3B is involved in processing of S1 in the present embodiment.

Figure 13:
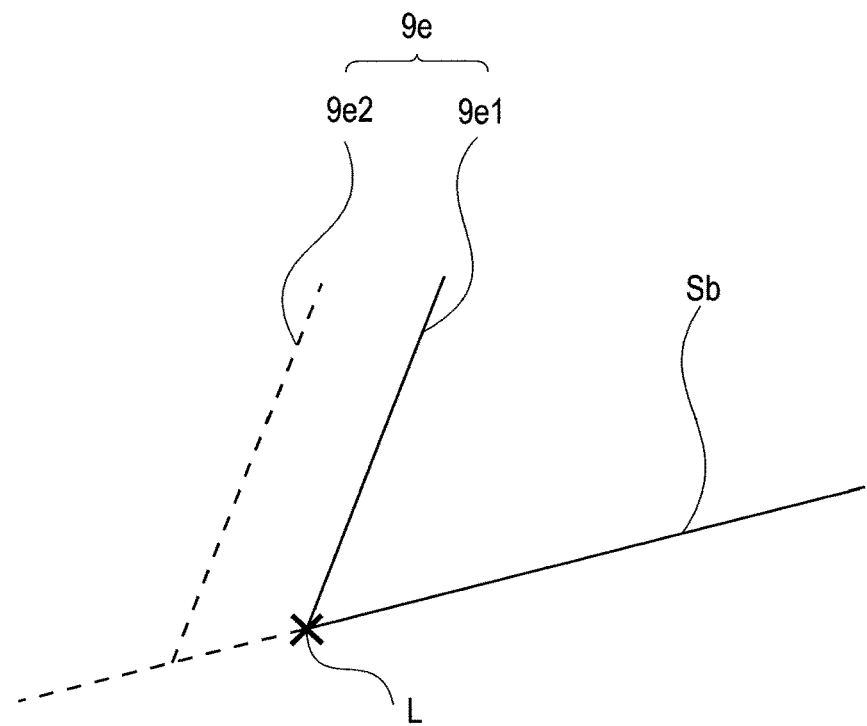
FIG. 13 is a schematic view explaining an axis 9a estimation position of an insertion portion 9 according to the fourth embodiment.

FIG. 13 is a schematic view explaining an axis 9a estimation position of the insertion portion 9 according to the fourth embodiment. The surface data analysis unit 32A4 acquires 3D surface data of an object. Based on the surface data, an edge in a longitudinal direction of the insertion portion 9 of the endoscope 2 is extracted. In FIG. 13, of an edge 9e of the insertion portion 9, an edge 9e1 that can be acquired as the surface data is shown by a solid line, and an edge 9e2 that cannot be acquired as the surface data is shown by a broken line. In the present embodiment, the edge 9e1 in the longitudinal direction of the insertion portion 9 extracted from the surface data is estimated as the axis 9a of the insertion portion 9.

Figure 14:
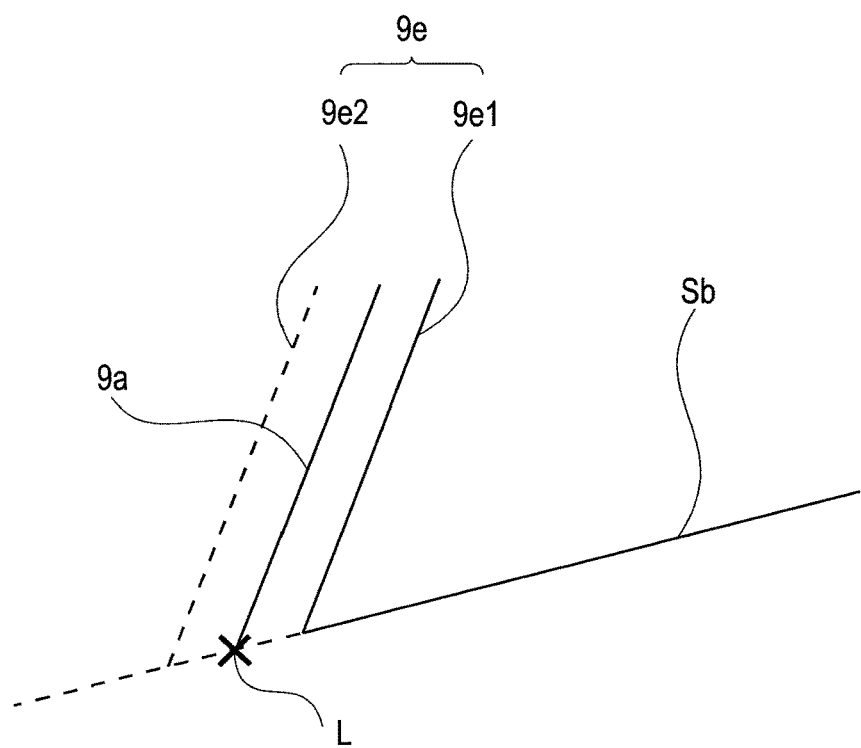
FIG. 14 is a schematic view explaining another estimation position of an axis 9a of the insertion portion 9 according to the fourth embodiment.

Note that a sectional shape of the insertion portion 9 is approximated to an ellipse, from surface data of a boundary of the insertion portion 9 and a body cavity, and a straight line that passes through a center of the approximated ellipse, and is parallel with the edge 9e1 in the longitudinal direction of the insertion portion 9 that is extracted from the surface data may be estimated as the axis 9a. FIG. 14 is a schematic view explaining another estimation position of the axis 9a of the insertion portion 9 according to the fourth embodiment. The sectional shape of the insertion portion 9 may be estimated from the surface data, or design data of the sectional shape of the insertion portion 9 may be stored in advance in a storage unit not illustrated and provided in the endoscope 2, and the design data may be referred to.

Subsequently, after the boundary of the insertion portion 9 and the body cavity is estimated (S2), estimation of the landmark is performed in S3. More specifically, an intersection point of a surface Sb extracted as the body cavity (for example, a stomach wall) from the 3D surface data of the object, and the axis 9a estimated in S1 is estimated as a landmark L.

As above, according to the present embodiment, it is also possible to obtain a similar effect to the effect of the first embodiment.

Fifth Embodiment

In a present embodiment, a lesion part in a body cavity is detected, and a distance between the landmark estimated in the aforementioned respective embodiments and the lesion part is calculated. An endoscope apparatus of the present embodiment has similar components to the components of the endoscope apparatus 1 of the first embodiment, the same components will be assigned with the same reference signs, and explanation will be omitted. Hereinafter, a configuration of an arithmetic operation unit 22b different from the first embodiment will be described.

Figure 15:
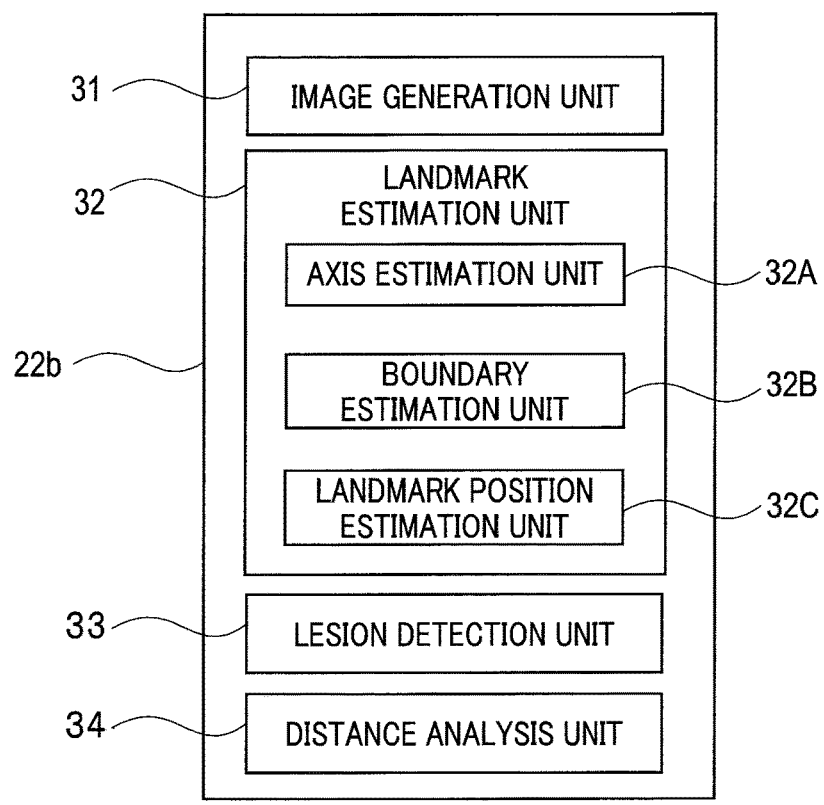
FIG. 15 is a block diagram illustrating a configuration of an arithmetic operation unit 22b of a control arithmetic operation unit 22 according to a fifth embodiment.

FIG. 15 is a block diagram illustrating the configuration of the arithmetic operation unit 22b of a control arithmetic operation unit 22 according to a fifth embodiment of the present invention. The arithmetic operation unit 22b of the present embodiment has a lesion detection unit 33 and a distance analysis unit 34 in addition to an image generation unit 31, and a landmark estimation unit 32.

The lesion detection unit 33 performs processing of applying an image discriminator that acquires a function of being able to discriminate a tumor (polyp) image in advance by a learning method such as deep learning to an endoscope image, and thereby detects a lesion part from the image. Note that for detection of a lesion part, other methods may be used without being limited to the learning method described above. For example, polyp candidate detection processing as disclosed in Japanese Patent Application Laid-Open Publication No. 2007-244518 or the like may be used.

The distance analysis unit 34 calculates a distance between a lesion part and a landmark. Note that the distance between two points may be calculated as a direct distance, or when 3D surface data of an object can be acquired, a creepage distance along a surface of an inside of a body cavity (3D surface data) may be obtained.

Figure 16:
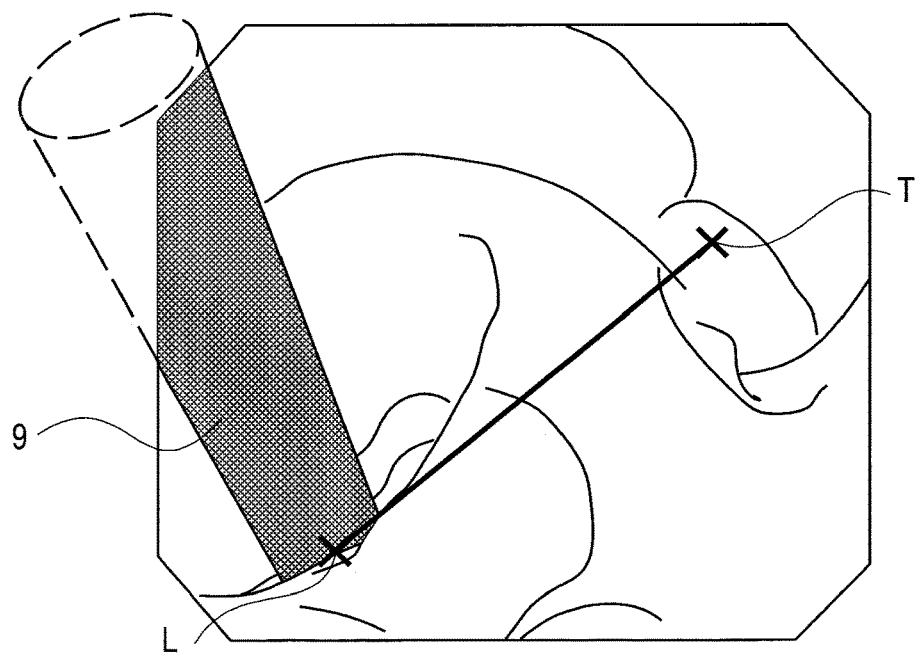
FIG. 16 is a schematic view showing a direct distance between a landmark and a lesion part.
Figure 17:
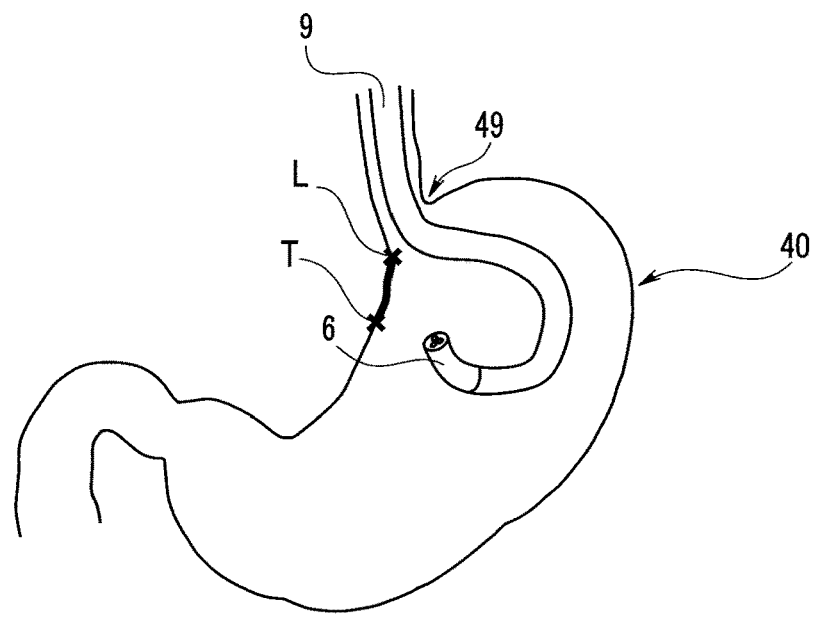
FIG. 17 is a schematic view showing a creepage distance between the landmark and the lesion part.

FIG. 16 is a schematic view showing a direct distance between the landmark and the lesion part. When the direct distance is calculated, the distance analysis unit 34 connects an estimated landmark L and a detected lesion part T by a straight line as illustrated in FIG. 16, and calculates a distance between the landmark L and the lesion part T. FIG. 17 is a schematic view showing a creepage distance between the landmark and the lesion part. When the creepage distance is calculated, the distance analysis unit 34 connects the estimated landmark L and the detected lesion part T by a straight line as illustrated in FIG. 17, and calculates a distance between the landmark L and the lesion part T.

As above, according to the estimating method of the present embodiment, it is possible to obtain a similar effect to the effect of the first embodiment, and it is possible to measure the distance from the lesion part by using a position of the estimated landmark, and generate and present useful information for a procedure of a surgeon.

Sixth Embodiment

In the aforementioned embodiment, estimation of the landmark is performed regardless of the state of the endoscope, but in a present embodiment, a bending state of an insertion portion 9 is detected, and estimation of a landmark is performed only when it is detected that the insertion portion 9 is bending. An endoscope apparatus of the present embodiment has similar components to the components of the endoscope apparatus 1 of the first embodiment except for means that detects bending of the insertion portion 9 provided in an endoscope 2, the same components will be assigned with the same reference signs, and explanation will be omitted.

Figure 18:
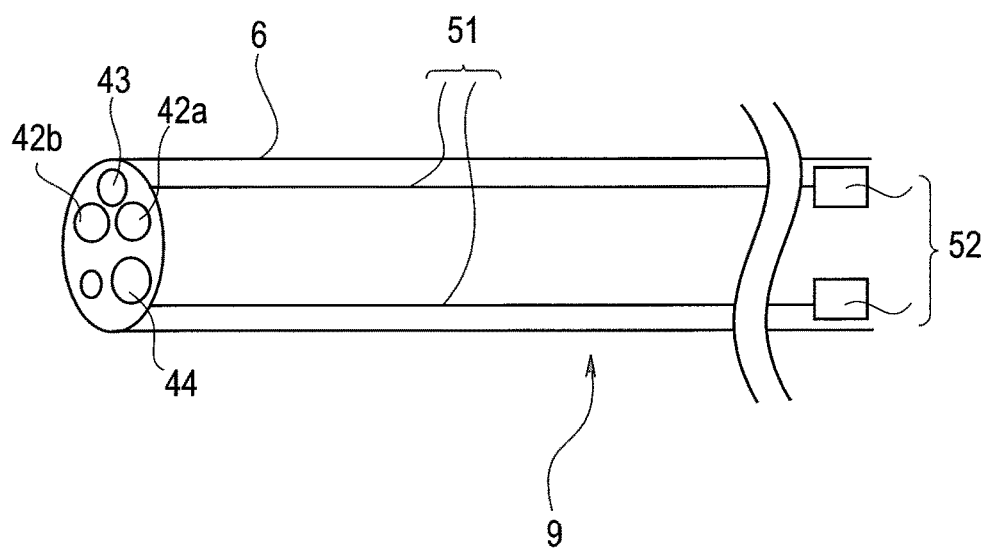
FIG. 18 is a schematic view explaining one example of a configuration of an endoscope 2 according to a sixth embodiment.

FIG. 18 is a schematic view explaining an example of a configuration of the endoscope 2 according to the present embodiment. In the endoscope 2 of the present embodiment, a wire 51 that causes the insertion portion 9 to bend is provided. One end of the wire is connected to a pressure sensitive apparatus 52. When a pressure is applied to the wire 51 to cause the insertion portion 9 to bend, the pressure sensitive apparatus 52 detects the pressure. A detection result by the pressure sensitive apparatus 52 is outputted to a control arithmetic operation unit 22. Note that means that detects bending of the insertion portion 9 is not limited to detection by the aforementioned pressure sensitive apparatus 52, but other means may be used.

The control arithmetic operation unit 22 executes respective processes in a landmark estimation unit 32 only when the pressure sensitive apparatus 52 detects a wire pressure. Note that based on the wire pressure detected by the pressure sensitive apparatus 52, a bending angle of the insertion portion 9 may be estimated, and may be used in estimation of an axis 9a of the insertion portion.

As above, according to the aforementioned respective embodiments and modifications, it is possible to estimate the position of the landmark with high precision even when the landmark is shielded and cannot be specified directly as the measurement point because the insertion portion itself is reflected in the endoscope image as a result that the endoscope insertion portion is bent.

The present invention is not limited to the aforementioned embodiments, and it goes without saying that various modifications and applications are possible within the range without departing from the gist of the invention.

What is claimed is:

1. A landmark estimating method for estimating a position of a landmark that is a hole existing in an object and is a site through which an insertion portion penetrates, in an endoscope image obtained by picking up an image of the object by an endoscope with the insertion portion bent, the method comprising:
   estimating an axis of the insertion portion;
   estimating a boundary of the insertion portion and the object; and
   estimating the position of the landmark based on the axis and the boundary.

2. The landmark estimating method according to claim 1, wherein the axis is estimated by extracting an entity that is used in estimation of the axis from the endoscope image by color analysis of the endoscope image, and analyzing a shape of the entity.

3. The landmark estimating method according to claim 2, wherein the entity is an edge of the insertion portion.

4. The landmark estimating method according to claim 2, wherein the entity is a marker provided on the insertion portion.

5. The landmark estimating method according to claim 2, wherein a specular reflection portion of the insertion portion is extracted by luminance analysis of the endoscope image, and a center region of the insertion portion in which the axis exists is estimated.

6. The landmark estimating method according to claim 1, wherein 3D surface data of the object is acquired, and an edge in a longitudinal direction of the insertion portion that is extracted from the 3D surface data is estimated as the axis.

7. The landmark estimating method according to claim 6, wherein a sectional shape of the insertion portion is approximated to an ellipse from 3D surface data of a boundary of the insertion portion and the object, and a straight line that passes through a center of the ellipse and is parallel with the edge in the longitudinal direction of the insertion portion that is extracted from the 3D surface data of the object is estimated as the axis.

8. The landmark estimating method according to claim 7, wherein an intersection point of the estimated axis and the 3D surface data of the object is estimated as the landmark.

9. The landmark estimating method according to claim 6, further comprising:
    detecting a lesion part from the object, and calculating a distance from the landmark to the lesion part.

10. The landmark estimating method according to claim 9,
    wherein the distance is a creepage distance along the 3D surface data of the object.

11. The landmark estimating method according to claim 1, wherein a bending state of the insertion portion is detected, and estimation of the axis is performed only when it is detected that the insertion portion is bending.

12. A processor configured to estimate a position of a landmark that is a hole existing in an object, and is a site through which an insertion portion penetrates, in an endoscope image obtained by picking up an image of the object by an endoscope with the insertion portion bent, the processor comprising:
    an axis estimation circuit configured to estimate an axis of the insertion portion;
    a boundary estimation circuit configured to estimate a boundary of the insertion portion and the object; and
    a landmark position estimation circuit configured to estimate the position of the landmark based on the axis and the boundary.

13. A non-transitory computer-readable storage medium storing a program,
    the program being a program configured for estimating a position of a landmark that is a hole existing in an object, and is a site through which an insertion portion penetrates, in an endoscope image obtained by picking up an image of the object by an endoscope with the insertion portion bent, the program being configured to cause a computer to:
    estimate an axis of the insertion portion,
    estimate a boundary of the insertion portion and the object, and
    estimate the position of the landmark based on the axis and the boundary.

* * * * *